US009400260B2

(12) United States Patent
Suh et al.

(10) Patent No.: US 9,400,260 B2
(45) Date of Patent: Jul. 26, 2016

(54) PREFABRICATED, SELF-CONTAINED GEL ELECTROPHORESIS MODULE

(71) Applicants: Man-Hee Suh, Freeville, NY (US); Valentin Petrov, Union City, CA (US)

(72) Inventors: Man-Hee Suh, Freeville, NY (US); Valentin Petrov, Union City, CA (US)

( * ) Notice: Subject to any disclaimer, the term of this patent is extended or adjusted under 35 U.S.C. 154(b) by 71 days.

(21) Appl. No.: 14/273,508

(22) Filed: May 8, 2014

(65) Prior Publication Data
US 2014/0332390 A1    Nov. 13, 2014

Related U.S. Application Data

(60) Provisional application No. 61/822,371, filed on May 11, 2013.

(51) Int. Cl.
*G01N 27/447* (2006.01)
*G01N 27/453* (2006.01)

(52) U.S. Cl.
CPC .... *G01N 27/44713* (2013.01); *G01N 27/44756* (2013.01); *G01N 27/44773* (2013.01)

(58) Field of Classification Search
CPC ............. G01N 27/44704; G01N 27/44756; G01N 27/44773; G01N 27/44778; G01N 27/44782; G01N 27/453
See application file for complete search history.

(56) References Cited

U.S. PATENT DOCUMENTS

| 4,284,491 | A | * | 8/1981 | Vesterberg | B01D 57/02 204/606 |
|---|---|---|---|---|---|
| 4,975,174 | A | * | 12/1990 | Bambeck | G01N 27/44756 204/618 |
| 5,582,702 | A | * | 12/1996 | Cabilly | B01D 57/02 204/456 |
| 5,709,788 | A | * | 1/1998 | Chen | G01N 27/44704 204/466 |
| 5,888,369 | A | * | 3/1999 | Tippins | G01N 27/44708 204/456 |
| 2004/0079638 | A1 | * | 4/2004 | Rooney | C07K 1/26 204/450 |

FOREIGN PATENT DOCUMENTS

WO    WO 98/27420 A1 *  6/1998 ............. G01N 27/26

* cited by examiner

*Primary Examiner* — Alexander Noguerola
(74) *Attorney, Agent, or Firm* — Weigue Zhou

(57) ABSTRACT

An electrophoresis system is provided. The system includes a buffer chamber box having a front surface. The buffer chamber box is divided into a first chamber and a second chamber by a divider. The system also includes a gel plate. A gel chamber is formed by the gel plate and the front surface of the buffer chamber box. The first chamber has a first electrode and a first conductive path member. The second chamber has a second electrode and a second conductive path member.

21 Claims, 10 Drawing Sheets

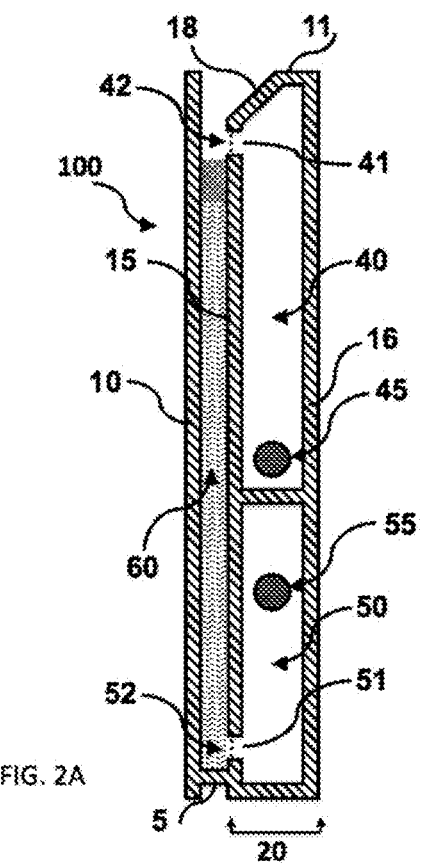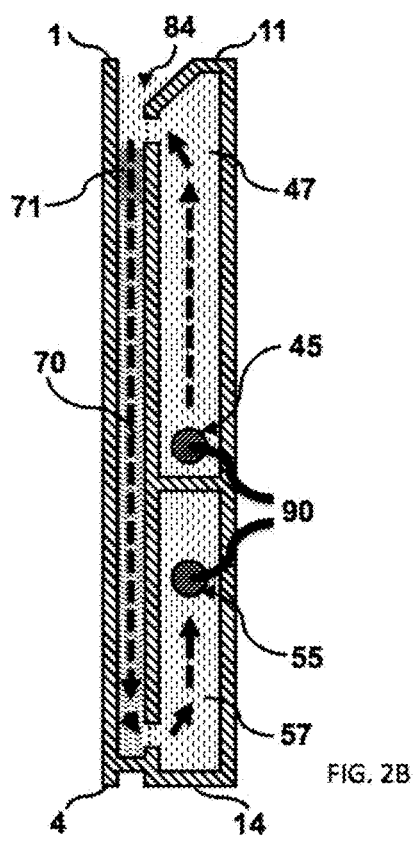

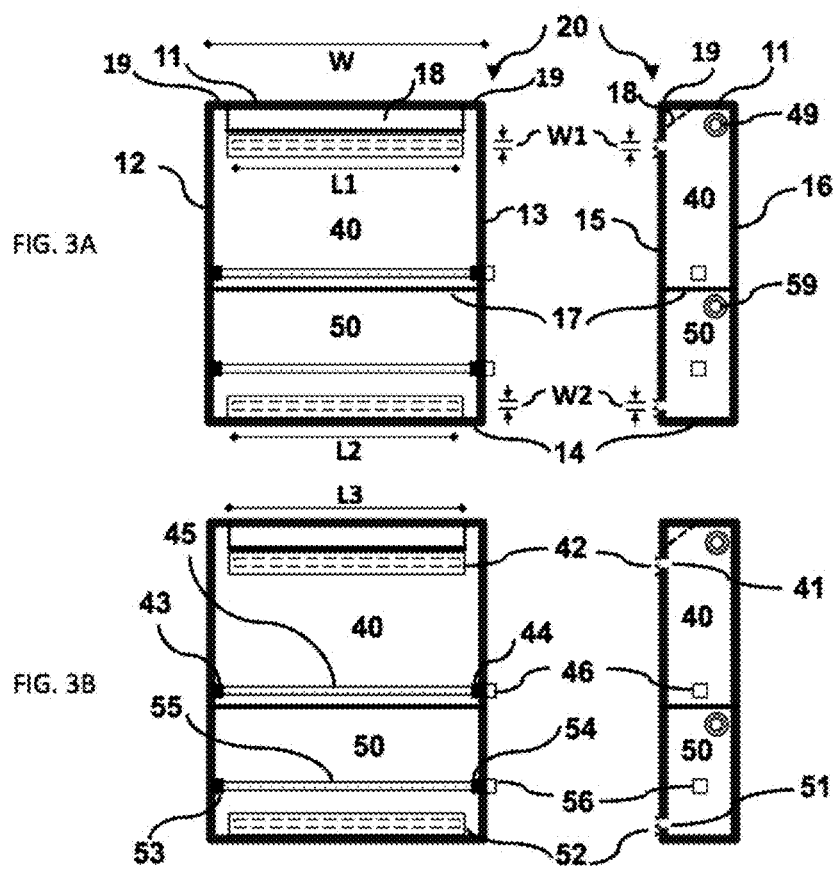

PREFABRICATED, SELF-CONTAINED GEL ELECTROPHORESIS MODULE

CROSS REFERENCE TO RELATED APPLICATIONS

This application claims the priority benefit of the U.S. Provisional Patent Application Ser. No. 61/822,371 filed on May 11, 2013, the entire contents of which are hereby incorporated by reference.

FIELD OF INVENTION

This invention relates generally to a gel electrophoresis module system and a method for using the same, and more specifically, a ready-to-use gel electrophoresis module system and an electrophoresis method for using the same.

BACKGROUND

Gel electrophoresis is a widely used technique for separating, analyzing, and purifying various biological molecules such as deoxyribonucleic acid (DNA), ribonucleic acid (RNA), polypeptides, proteins, and also nanoparticles, and other materials. As such, gel electrophoresis is extensively employed in many fields, for example biotechnology, molecular biology, biochemistry, medicine, pharmaceutical sciences, fisheries sciences, veterinary medicine, nanotechnology, and other fields.

In gel electrophoresis, an electric field is applied to move molecules through gel matrix, and the electrophoretic mobility of each molecule depends not only on its charge, size, and shape, but also on the physicochemical properties of a gel matrix such as pH value, salts composition, and the pore size of the gel matrix. Therefore, it is desirable for successful gel electrophoresis system to produce consistent gel matrices to separate molecules.

In conventional vertical gel electrophoresis, a cassette is assembled in upright position to house a buffered gel matrix between two flat plates, typically transparent glass plates or plastic plates. To prepare a gel, the two plates are separated by spacers arranged along the plate edges of two opposite sides. The bottom of cassette is sealed either by placing on the rubber gaskets of casting stands or by using other means, such as additional spacer, tape, agarose, or petroleum based material, followed by preparation and casting of buffered gel matrix. The gel matrix is made of a type of cross-linked polymer, usually polyacrylamide or agarose, and has wells for holding the samples to be analyzed. Care must be practiced during cassette assembly to prevent the gel matrix leakage. The whole procedures are labor intensive, time consuming, and error prone and involve using hazardous chemicals such as polyacrylamide and TEMED (Tetramethylethylenediamine). At the end of electrophoresis, the gel matrix is removed for subsequent analysis, and all components of the cassette must be thoroughly washed for reuse. Additionally, there is an incurring cost of replacing damaged or misplaced components of the cassette.

Alternatively, pre-cast gels enclosed in plastic cassettes produced by manufacturers can be purchased for gel electrophoresis. Regardless of whether pre-cast gels or self-made gels are used, an electrophoresis system apparatus with specific configuration must be used to accommodate the particular dimension of gel cassettes. Once the gel cassette is assembled into the electrophoresis system apparatus, a buffer solution is filled into two reservoirs in the apparatus to make contacts with the top and bottom of the gel matrix. After sample loading, the electrophoresis system apparatus delivers electrical current coming from a power supply through the gel matrix by using two electrodes in the buffers. Even though there are several electrophoresis system apparatus designs, all apparatuses essentially provide two reservoirs for a buffer solution(s) and have a platinum (or other metals or alloys of the platinum metal group) electrode in each reservoir. These electrophoresis system apparatuses are expensive, need a large amount of buffer to run, demand constant maintenance such as washing, and require a specific dimension of the gel cassettes, both pre-cast gels and self-made gels.

U.S. Pat. No. 8,361,293 B2 and U.S. Pat. No. 8,361,294 B2 describe a monolithic electrophoresis gel system, one-piece electrophoresis apparatuses that can be used directly without assembly or modification. However, the all-in-one unit requires an additional device in form of a lid that must be in specific dimension to fit on the top surface of the units. In addition to limiting user choice, the lid is suggested to have electrodes made of an electrically conductive material such as platinum, titanium, platinized titanium, and the like. The monolithic electrophoresis gel system uses an additional apparatus to provide an electrical current, just like current electrophoresis system apparatuses; it locks users into using a preset combination, puts extra cost, and loads additional handing step and maintenance. The monolithic electrophoresis gel system may have the advantage over current electrophoresis system apparatuses using pre-cast gels in that the monolithic electrophoresis gel system supplied with buffer.

These systems as disclosed in the prior art references usually require additional apparatus or components, and thus not fully independent. Generally, external electrodes need to be supplied at the point of the electrophoresis. Furthermore, these systems as disclosed do not provide a fully prefabricated gel electrophoresis module, which is self-contained and ready for electrophoresis.

Consequently, there is a need for a pre-cast gel electrophoresis system that is low cost, maintenance free, and ready-to-use without dependence on an additional form of apparatus. Such self-contained gel electrophoresis system can be manufactured in any dimensions, hence further expanding gel electrophoresis technique applications such as mobile capacity (use outside of typical laboratory settings) and high-throughput screening capability (large sample number screening).

BRIEF SUMMARY OF THE DISCLOSURE

It is an objective of this invention to provide a ready-to-use prefabricated gel electrophoresis module.

It is an objective of this invention to provide a gel electrophoresis module that can be used in a ready-to-use gel electrophoresis system.

It is also an objective of this invention to provide an electrophoresis method using a ready-to-use prefabricated gel electrophoresis module.

It is a further objective of this invention to provide a ready-to-use prefabricated gel electrophoresis module that can be used directly without assembly or modification thereto.

It is yet another objective of this invention to provide a ready-to-use prefabricated gel electrophoresis module that reduces handing, preparation for use in electrophoresis, and maintenance.

It is a still further objective of this invention to provide a ready-to-use prefabricated gel electrophoresis module that can be manufactured in any dimension to accommodate various sample numbers to be analyzed.

It is a still further objective of this invention to provide a ready-to-use prefabricated gel electrophoresis module that can be custom manufactured for specific applications.

This disclosure describes a gel electrophoresis module that may achieve one or more of the above mentioned and other objectives. This disclosure is directed to a self-contained gel electrophoresis module for use in performing gel electrophoresis.

One aspect of the present disclosure provides a gel electrophoresis system for performing gel electrophoresis. The system includes a buffer chamber box having a front surface. The buffer chamber box is divided into a first chamber and a second chamber by a divider. The system also includes a gel plate. A gel chamber is formed by the gel plate and the front surface of the buffer chamber box. The first chamber has a first electrode and a first conductive path member. The second chamber has a second electrode and a second conductive path member.

Another aspect of the present disclosure provides a gel electrophoresis system for performing gel electrophoresis. The system includes a first chamber having a first electrode and a first conductive path member on a first front surface. The system also includes a second chamber having a second electrode and a second conductive path member on a second front surface. A gel chamber is formed by the first front surface and the second front surface.

Other aspects of the present disclosure can be understood by those skilled in the art in light of the description, the claims, and the drawings of the present disclosure.

BRIEF DESCRIPTION OF THE DRAWINGS

FIG. 2A illustrates the cross-section view of an exemplary gel electrophoresis module consistent with the disclosed embodiments;

FIG. 2B illustrates the cross-sectional view of an exemplary gel electrophoresis module system showing the current flow in the exemplary module system consistent with the disclosed embodiments;

FIGS. 3A and 3B illustrate front and side views of an exemplary buffer chamber box consistent with the disclosed embodiments;

DETAILED DESCRIPTION

Figure 1:
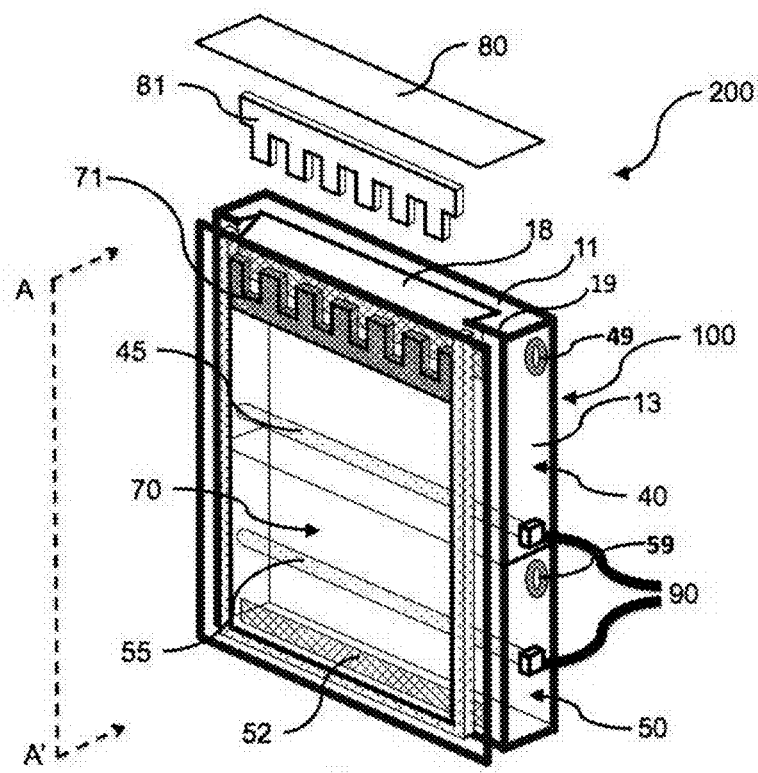
FIG. 1 illustrates a perspective view of an exemplary gel electrophoresis module system consistent with the disclosed embodiments.

In describing the preferred embodiments of this invention, reference will be made herein to FIGS. 1-13 of the drawings, wherein like reference numerals designate to similar features of this invention. Throughout this description, the embodiments shown should be considered as exemplars, rather than as limitations on the present invention. Furthermore, features of this invention are not necessarily shown to scale in the drawings.

The present disclosure describes modules, apparatus, systems, and methods for executing gel electrophoresis using an exemplary ready-to-use gel electrophoresis module consistent with the disclosed embodiments. The disclosed system may be disposable and may be manufactured with certain components combined into a single module, which may include a first chamber and a second chamber, each containing an electrode and being configured to contain a buffer solution, and a gel chamber being configured to contain a pre-cast gel. The system consistent with the disclosed embodiment may not require additional components except for power connector and may be ready to be connected to power supply for electrophoresis.

FIGS. 1, 2A and 2B illustrate an exemplary gel electrophoresis module system 200 consistent with the disclosed embodiments. As shown in FIGS. 1, 2A and 2B, the system 200 may include a module 100. The module 100 may include a first chamber 40, a second chamber 50, and a gel chamber 60. The chambers 40 and 50 may contain buffer solutions 47 and 57, respectively, for electrophoresis. The chambers 40 and 50 may also include electrodes 45 and 55, respectively. In certain embodiments, the electrodes 45 and 55 are carbon electrodes. The electrodes 45 and 55 may be made of other suitable materials. In certain embodiments, the electrodes 45 and 55 are embedded in the chambers 40 and 50, respectively. The system 200 may include a pre-cast first gel matrix 70 in the gel chamber 60. The system 200 may also include power cables 90 that electrically connect the module 100 to a power source (not shown). The top surface of the module 100 may be sealed with a seal 80. The seal 80 may be a removable tape seal that prevents leakage of a buffer solution 84 covering a comb 81. The seal 80 may also be other suitable material to prevent leakage of buffer solution.

FIG. 2A illustrates the cross-sectional view of the module 100 along the line A-A' in FIG. 1. As shown in FIG. 2A, the first chamber 40 is above the second chamber 50, and the stacked chambers 40 and 50 are adjacent to the gel chamber 60. The features to module 100 may include: i) the electrodes 45 and 55 inside the first chamber 40 and second chamber 50, respectively; and ii) a conductive path member 42 residing over a first opening 41 of the first chamber 40, and a conductive path member 52 residing over a second opening 51 of the second chamber 50. The electrodes 45 and 55 may be integrated in the chambers 40 and 50, respectively. In certain embodiments, the electrodes 45 and 55 may be made of a carbon material. In certain material, the carbon material may be graphite, graphite ink, graphene, or graphene ink. Any other appropriate material may be used to make the electrodes 45 and 55.

In certain embodiments, the conductive path members 42 and 52 are membranes, however, the conductive path members 42 and 52 may also be made of other suitable materials. The conductive members 42 and 52 may also be integrated into the chambers 40 and 50. The opening 41 may be a narrow slit and located near the top edge of the first chamber 40; the opening 51 may be a narrow slit and located near the bottom edge of the second chamber 50. As shown in FIGS. 3A and 3B, the length L1 of the opening 41 and the length L2 of opening 51 may be slightly shorter than the width dimension W of the chambers 40 and 50.

FIG. 2B illustrates the flowing of the electric current during an electrophoresis using the module system 200. As shown in FIG. 2B, the system 200 may include the enclosed buffers 47 and 57 within the first chamber 40 and second chamber 50, respectively, and the pre-casted first gel matrix 70. The first gel matrix 70 may be a separating gel matrix composed of any gel suitable for gel electrophoresis, including, but not limited to polyacrylamide gels or agarose gels. The buffer used for making the first gel matrix 70 and the concentrations of the gel materials depend on the target samples to be analyzed. Also, on the top of the first gel matrix 70, there may be a second gel matrix 71. The composition of the second gel matrix 71 may or may not be different to that of the first gel matrix 70. In certain embodiments, the second gel matrix 71 is a stacking gel matrix. In certain embodiments, the concentrations of one or more components of the first gel matrix 70 may change from top to bottom to form a gradient gel. In certain embodiments, the concentrations of one or more components of the second gel matrix 71 may change from top to bottom to form a gradient gel.

As shown in FIG. 2B, during electrophoresis, an electrical charge from the power cable 90 is applied to the electrode 45, whereby the electrical current flows from the buffer 47 in the first chamber 40 through the first gel matrix 70 (and a second gel matrix 71 if present), into the buffer 57 in the second chamber 50, and to the electrode 55 coming back to the power cable 90 to form a circuit. The direction of the electricity flow may also be reversed.

Returning to FIG. 2A, the module 100 may be a one-piece electrophoresis box, which may be made of a material with certain rigidity, such as a plastic (e.g., acrylic or styrene plastics) or a glass material. Other suitable materials may also be used. The module 100 may include a buffer chamber box 20 and a gel plate 10. The buffer chamber box may have a front surface 15. The front surface 15, the gel plate 10, and an embossed ridge 5 may form the gel chamber 60.

FIGS. 3A and 3B illustrate the buffer chamber box 20 consistent with the disclosed embodiments. As shown in FIGS. 3A and 3B, the buffer chamber box 20 may substantially resemble a rectangular cuboid. The buffer chamber box 20 may be in other suitable shapes. A beveled surface 18 may be shaped at an edge 19 formed by the front surface 15 and a top surface 11. As shown in FIGS. 3A-4B, the length dimension L3 of the surface 18 may be shorter than the width W of the buffer chamber box 20, leaving the both ends of the edge 19 a substantially right angle formed by the front surface 15 and the top surface 11. Returning to FIG. 3A, the first chamber 40 may be enclosed by the top surface 11, two side surfaces 12 and 13, the front surface 15, a back surface 16, the surface 18, and a buffer chamber divider 17, and the second chamber 50 may be enclosed by the two side surfaces 12 and 13, the front surface 15, the back surface 16, the buffer chamber divider 17 and a bottom surface 14. The buffer chamber 20 may be manufactured as an integrated unit. The first chamber 40 may have a first venting opening 49 and the second chamber 50 may have a second venting opening 59. The venting openings 49 and 59 may connect the space inside the chamber with the ambient environment.

As shown in FIG. 3B, the two openings 41 and 51 are located on the front surface 15 of the buffer chamber box 20. The opening 41 may be located near the top edge of the front surface 15 below the beveled surface 18, whereas the opening 51 may be located inward of the front surface 15 near the bottom surface 14. The openings 41 and 51 may also be located at any suitable locations on the front surface 15. In certain embodiments, the lengths of the openings 41 and 51, L1 and L2, may be nearly the same as the length of the beveled surface 18, L3. The lengths of the openings 41 and 51, L1 and L2, may also be different to the length of the beveled surface 18, L3. In certain embodiments, as shown in FIG. 3A, the width of the opening 41, W1, and the width of the opening 51, W2, may be about 1 mm to 1.5 mm. Other width may also be used.

Figures 4A, 4B:
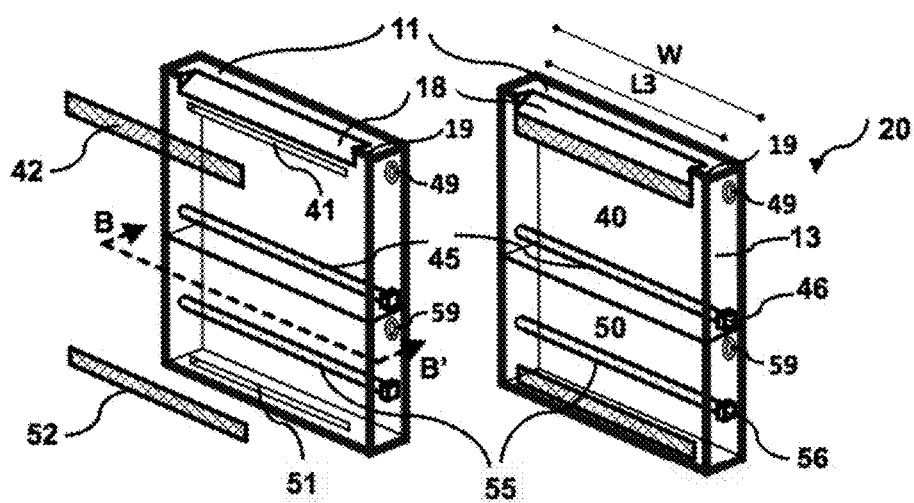
FIGS. 4A and 4B illustrate perspective views showing openings in the buffer chambers and electrically conductive path members of an exemplary system consistent with the disclosed embodiments.

FIGS. 4A and 4B illustrate a perspective view of the buffer chamber box 20 consistent with the disclosed embodiments. As shown in FIGS. 4A and 4B, the openings 41 and 51 may be covered with electrically conductive path members 42 and 52, respectively. The conductive path members 42 and 52 establish electrical communication between the first gel matrix 70 (and the second gel matrix 71 if used) and the buffers 47 and 57. In certain embodiments, the conductive path members 42 and 52 may be made of membranes. The conductive path members 42 and 52 may also be manufactured as an integral part of the front surface 15 using multi-material molding (multi-shot injection molding) or any other suitable methods in place of the openings 41 and 51 (or mechanically connected or glued).

The membranes 42 and 52 may prevent the first gel matrix 70 (and the second gel matrix 71 if used) from entering the second chamber 50 and/or the first chamber 40 during the polymerization of the first gel matrix 70 and/or the second gel matrix 71. The membranes 42 and 52 may be partially permeable, allowing water and the molecules smaller than their pore sizes to pass. The passing of water and small molecules of the membranes 42 and 52 may be slow enough so that no significant amount of the first gel matrix 70 and/or the second gel matrix 71 may pass through the membranes 42 and 52 during the polymerization period of the first gel matrix 70 and/or the second gel matrix 71. The membranes 42 and 52, being partially permeable, permit the electricity flow freely through the membranes during electrophoresis.

In certain embodiments, the membrane 52 resides between the first gel matrix 70 and the buffer 57 inside of the second chamber 50, whereas the membrane 42 does not make a direct contact with the top of the first gel matrix 70 (or the second gel matrix 71 if used). The top of the first gel matrix 70 or the second gel matrix 71 may be just below the opening 41.

The membranes 42 and 52 may be applied to the openings 41 and 51 from either the inside or the outside of the first chamber 40 and the second chamber 50, respectively. The membranes 42 and 52 may also be glued along the inside edges of the openings 41 and 51. The membranes 42 and 52 may be made of a tape seal specially designed to have a membrane material in the middle and an adhesive material along the edges, and the membranes 42 and 52 can be applied inside or outside of the first chamber 40 and second chamber 50.

The membranes 42 and 52 may be a type of semi- or partially permeable membrane, which may be made from regenerated cellulose or cellophane, and any suitable material, including special membranes designed for microfiltration, ultrafiltration, reverse osmosis, and nanofiltration. The membranes 42 and 52 may also keep the buffers inside of the first chamber 40 and the second chamber 50 even after the removal of the gel chamber 60 to retrieve the first gel matrix 70.

Therefore, the membranes 42 and 52 may prevent significant spillage during and after the electrophoresis because users only need to be concerned about handling the small volume of buffer 84 residing above a comb 81 as shown in FIG. 2B. Accordingly, gel electrophoresis module 100 is suitable for working with hazardous materials such as radioactive and biohazard materials because the module 100 may be used easily and cleanly, and may be safely disposed.

As shown in FIGS. 3A-5, both the first chamber 40 and the second chamber 50 include the electrodes 45 and 55, respectively. In certain embodiments, the electrodes 45 and 55 are made of graphite. Graphite is a form of carbon, chemically inert to many chemicals, is a stable form of carbon, has high melting point, and conducts electric current well. The cost of graphite electrode is also significantly lower than that of the precious metal electrodes, such as platinum, that are commonly used in the electrophoresis device on the current market. In other embodiments, the electrodes are made of other forms of carbon, such as carbon fiber. In yet other embodiments, the electrodes are made of carbon nanoparticles. In yet other embodiments, the electrodes are made from graphite. In yet other embodiments, the electrodes are made of chemically inert noble metals or noble metal alloys, such as gold or metals from the platinum group—platinum, osmium, iridium, ruthenium and rhodium and palladium or their alloys. In yet other embodiments, the electrodes are made of chemically inert base metal alloys, such as stainless steel. Other suitable materials may also be used to make the electrodes 45 and 55.

The module 100 may be manufactured in any dimensions without the need of an additional apparatus being in specific dimension to provide external electrodes at the point of the electrophoresis. For example, the module 100 can be manufactured with a large width dimension, such as about 100 cm, to accommodate a large number of samples (e.g. 100 or more) at once, which is useful for high-throughput screening purposes. Likewise, the module 100 can also be manufactured with a small width dimension, such as about 2 cm, to analyze small number of samples (e.g. 3 samples or even one sample), which is ideal for mobile research purposes or mobile clinics. Using graphite electrode that is significantly cheaper than precious metals may facilitate the manufacture of the module 100 in variable sizes with minor cost increase.

In certain embodiments, the first electrode 45 may be embedded near the bottom of the first chamber 40 that is formed by the divider 17 while the second electrode 55 may be embedded a little above the middle of the second chamber 50. Such a configuration may reduce possible electrical interference caused by accumulations of gas by-products. The first electrode 45 and the second electrode 55 may be located in any appropriate locations. In certain embodiments, the first chamber 40 is the cathode chamber where the hydrogen gas is produced at the electrode 45 while the second chamber 50 is the anode chamber where the oxygen gas is produced at the electrode 55. When the direction of the electricity flow is reversed, the first chamber 40 is the anode chamber producing the oxygen gas, and the second chamber 50 is the cathode chamber producing the hydrogen gas. The first and second electrodes 45 and 55 may also be located at other suitable position to reduce the effects of gas generated during electrophoresis.

Figure 5:
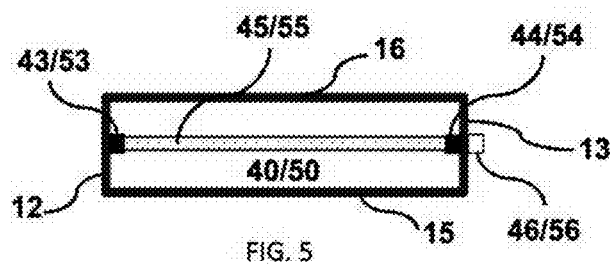
FIG. 5 illustrates a cross-sectional view along the line B-B' showing an electrode in the buffer chambers of an exemplary system consistent with the disclosed embodiments.

Referring to FIGS. 1-5, each of electrodes 45 and 55 extends in buffer chambers 40 and 50 from the sidewall 12 to the sidewall 13 of the buffer chamber box 20, respectively. As shown in FIGS. 3B and 5, flanges 43 and 44 secure the ends of the electrode 45, and flanges 53 and 54 secure the ends of the electrode 55. The flanges 43, 44, 53, and 54 may be molded as part of the buffer chamber box 20 during fabrication thereof. The electrodes 45 and 55 may also be securely inserted into recesses on the inner side of surface 12 and corresponding recesses on the inner side of surface 13. Other suitable mechanisms may be employed to secure the electrodes 45 and 55. The electrodes 45 and 55 may be protected by protective rods.

FIGS. 4B and 5 illustrate external leads 46 and 56 consistent with the disclosed embodiments. The external leads 46 and 56 are electrically connected to the electrodes 45 and 55. The external leads 46 and 56 may be connected to power source using a power connector (not shown) through the power cable 90. The power cable 90 with the connector may be provided as a component of the electrophoresis system 200. Or a user may choose the power cable 90 with the connector. The external leads 46 and 56 may be configured to accept different types of power connectors, such as plugs, clips, or any other suitable connectors. In some embodiments, the connectors are male banana plugs. In other embodiments, the connectors are banana jacks. In yet other embodiments, the connectors are conductive protrusions that can be used to come into contact with clips, such as alligator clips. In yet other embodiments, the connectors are clips that can be clipped to bare electrically energized wires. In other embodiments, the connectors are male BNC type connectors. In other embodiments, the connectors are female BNC type connectors.

In certain embodiments, the external leads 46 and 56 may be conductive leads, which may form integral parts of the module 100, coming in electrical contact with the electrodes 45 and 55. In certain embodiments, the short external leads 46 and 56 are fabricated with particular patterns, designs, or configuration, such as the asymmetrical plugs, short clips, rims, fittings, or other configuration, so that the electrical cables from the power supply can be connected to the short external leads 46 and 56 in such a way to only allow the electric flow in one direction to eliminate potential user error.

Figures 6A, 6B:
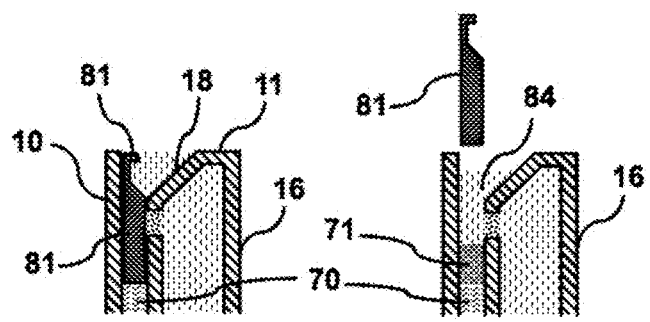
FIGS. 6A and 6B illustrate cross-sectional views showing a comb in the gel chamber of an exemplary system consistent with the disclosed embodiments.

FIGS. 6A and 6B illustrate the exemplary comb 81 consistent with the disclosed embodiments. As shown in FIGS. 1 and 6A, the comb 81 may be inserted into the top of first gel matrix 70 (or the second gel matrix 71 if used) to form one or more wells for sample-loading. As shown in FIG. 6B, the gel plate 10 and the beveled surface 18 form a space wherein the buffer 84 may reside to cover the top of the first gel matrix 70 (or the second gel matrix 71 if used).

Figures 7A, 7B:
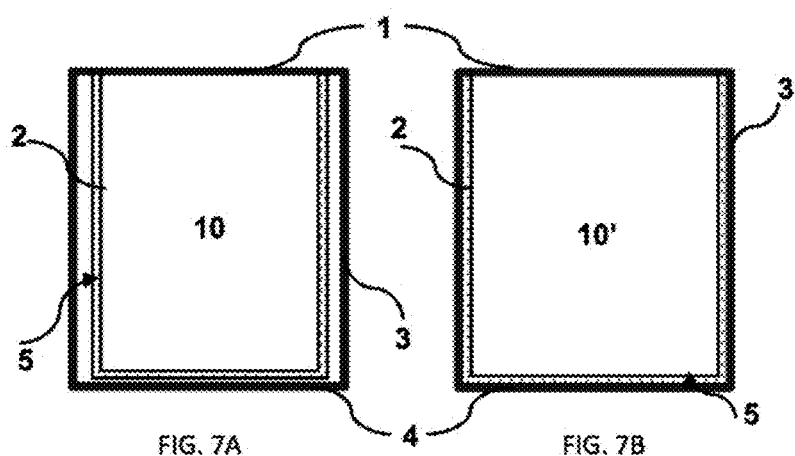
FIGS. 7A and 7B illustrate cross-sectional views showing a gel plate of an exemplary system consistent with the disclosed embodiments.
Figure 8:
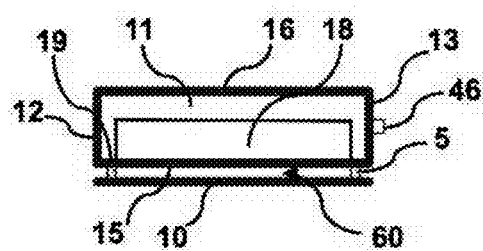
FIG. 8 illustrates a top view of an exemplary gel electrophoresis module consistent with the disclosed embodiments.
Figures 10A, 10B, 10C, 10D:
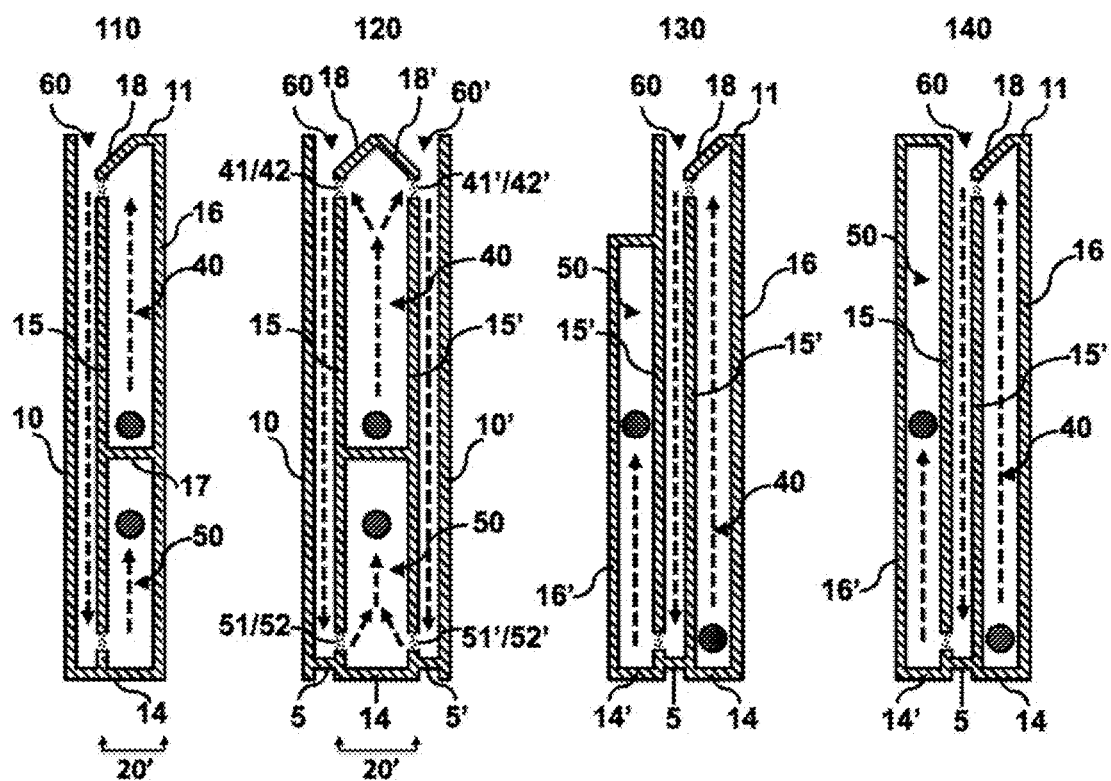
FIGS. 10A to 10D illustrate cross-sectional views of exemplary gel electrophoresis modules consistent with the disclosed embodiments.

FIGS. 7A to 8 illustrate an embossed ridge 5 in an exemplary module 100 consistent with the disclosed embodiments. As shown in FIG. 7A, the embossed ridge 5 may be integrally formed on the gel plate 10 facing the front surface 15 of the buffer chamber box 20. In certain embodiments, the embossed ridge 5 may be spaced a short distance inwardly from side edges 2, 3 and a bottom edge 4 of the gel plate 10. As shown in FIGS. 7B and 10A, in certain embodiments, the embossed ridge 5 may also be located along the side edges 2, 3 and the bottom edge 4 of the gel plate 10. The embossed ridge 5 may also be located on the front surface 15 of the buffer chamber box 20.

FIG. 8 illustrates a top view of the module 100 with the gel plate 10 attached to the buffer chamber box 20. As shown in FIG. 8, the gel plate 10, the front surface 15 of the buffer chamber box 20, and the embossed ridge 5 enclose the gel chamber 60. The embossed ridge 5 may attach the gel plate 10 and the buffer chamber box 20 using an ultrasonic welding, an adhesive seal, a sealant, or any other suitable mechanism to allow the gel plate 10 to be detachably attached to the buffer chamber box 20. Other suitable attachment mechanisms may also be used. The embossed ridge 5 may also be configured to allow the removal of the gel plate 10 from the buffer chamber box 20 without damaging the buffer chamber box 20. The embossed ridge 5 may also be configured to seal the gel chamber 60 to prevent the leakage of the buffer within the gel chamber 60.

Figure 9A:
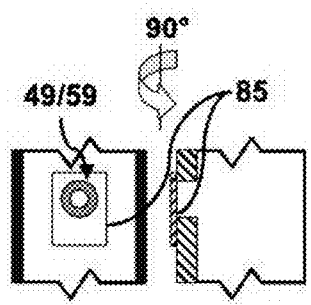
FIGS. 9A to 9C illustrate an exemplary venting system consistent with the disclosed embodiments.
Figure 9B:
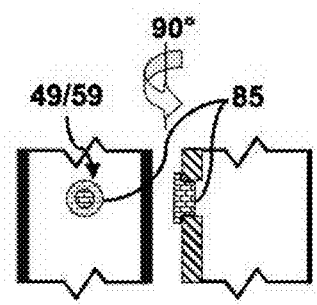
Figure 9C:
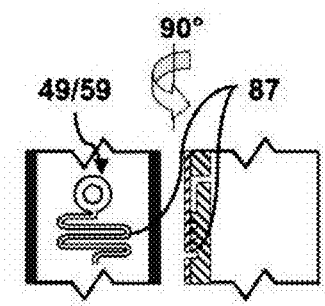

FIGS. 9A to 9C illustrate a venting system consistent with the disclosed embodiments. Shipping procedures such as air travel, or environmental changes such as weather temperature and pressure variations can lead to varying ambient pressures and temperatures. If this degree of expansion or contraction were to take place in a fixed volume, the chambers 40 and 50 holding the gases and liquid buffer would be stressed and tend to deform outward or inward to accommodate the expansion or contraction of the gases. This may warp the cassette and negatively impact the uniformities of the first gel matrix 70 and the gel chamber 60. In addition, during electrophoresis gases are being generated. It is desirable to vent the gases in the ambient surroundings to prevent the chambers 40 and 50 from expanding, which may cause damages to the module 100.

As shown in FIG. 9A, the venting system may be the openings 49/59, which may allow gases within the chamber to communicate with the ambient environment, thereby accommodating for expansion and contraction by substantially maintaining a pressure balance between the interior of the chambers 40 and 50 and the external environment. The venting openings 49 and 59 are configured to be sufficient to vent out gases being produced during electrophoresis. A stopper 85 may be placed on the venting openings 49 and 59 to prevent leakage if the module 100 is pre-filled with liquid. The stopper 85 may be removed or broken when the module 100 is ready for use. In certain embodiments, the stopper 85 is a seal as shown in FIG. 9A. The stopper 85 may also be a plug as shown in FIG. 9B. Any other suitable anti-leaking mechanism may also be used as the stopper 85.

Other venting system may also be used. As shown in FIG. 9C, in certain embodiments, the venting system is an opening 49/59 connected to a tube 87. The tube 87 opens to the ambient environment through the opening 49/59 at one end, and opens to the inside of the chamber 40/50 at another end. The venting opening 49/59 and the tube 87 allow for the gasses inside the chamber to equalize the pressure without letting the buffer solution to leak outwards. The cross section of the tube 87 is configured to be small enough and the tube 87 is configured to be long enough to prevent spillage of liquid by capillary forces, but the cross section is also configured to be large enough to allow all gasses to pass through in both directions. In certain embodiment, the tube 87 may have a circular cross section. The diameter of the tube 87 may be about 1 mm and the length may be about 50 mm. The tube 87 may have a cross section in other suitable shape and may also have other suitable size. The tube 87 may be straight or in other shapes. In certain embodiments as shown in FIG. 9C, the tube 87 may be spiral. In yet other embodiments the tube could be sinuous (labyrinthine). In some embodiments, the chambers could have only one vent. In other embodiments, the chambers could have multiple vents of different diameters, shapes and lengths.

FIGS. 10A to 10D illustrate different exemplary modules 110, 120, 130, and 140 consistent with the disclosed embodiments. As shown in FIG. 10B, the module 120 may have two gel chambers 60 and 60'. In this embodiment, the buffer chamber box 20' has four openings 41, 51, 41', and 51' covered with four membranes 42, 52, 42', and 52'; with two of the four openings on each side of the buffer chamber 20', whereby the two gel chambers 60 and 60' sandwich the buffer chamber 20'. In certain embodiments, the first chamber 40 and second chamber 50 can be rearranged. As shown in FIGS. 10C and 10D, in module 130 and module 140, the first chamber 40 may occupy one side of the gel chamber 60 whereas the second chamber 50 occupies the other side. With the second chamber 50 and first chamber 40 located on two sides of the gel chamber 60, the heat generated during electrophoresis may be distributed evenly. For the modules 130 and 140 as shown in FIGS. 10C and 10D, the surface 15 of the first chamber 40 and the surface 15' of the second chamber 50, and an embossed ridge 5 may form the gel chamber 60. The embossed ridge 5 may be formed on the surface 15 or 15'. As shown in FIG. 10 C, the second chamber 50 may have a smaller height to facilitate the sample loading process, as the top of the second chamber 50 does not obstruct the view of the sample wells.

Figure 11:
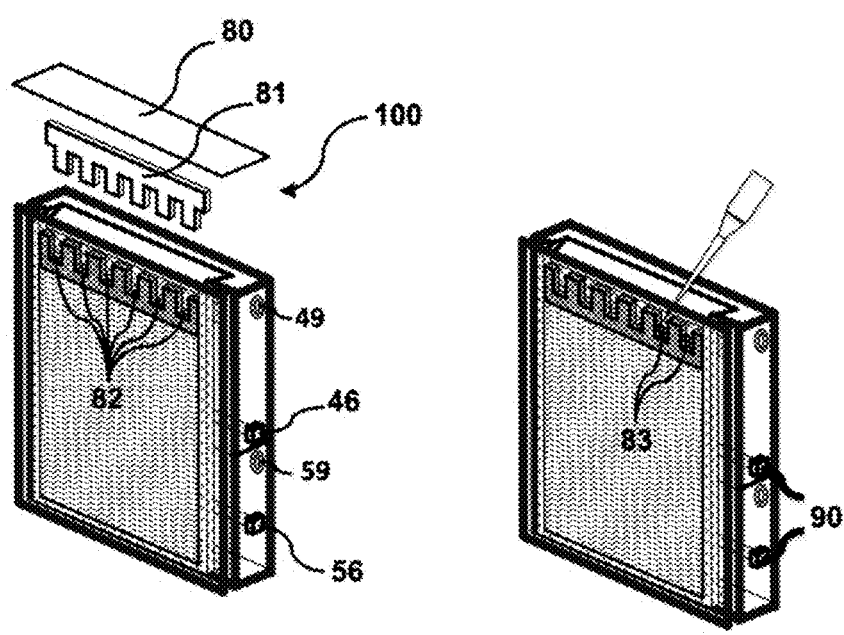
FIG. 11 illustrates a perspective view of an exemplary method of executing a gel electrophoresis using an exemplary gel electrophoresis module and system consistent with the disclosed embodiments.

FIG. 11 illustrates an exemplary gel electrophoresis using an exemplary module system 200. The seal 80 is removed from the top surface of the module 100. The comb 81 is removed to reveal sample wells 82, which are covered with the pre-loaded buffer 84 residing over the comb 81 as shown in FIGS. 1 and 2B. Target samples 83 are loaded into the sample wells 82. The sample wells 82 can be in the first gel matrix 70 or the second gel matrix 71.

After the sample-loading step, the electrical connection is established via the electrical cables 90 that may be specifically designed (or color coded) to directionally fit the external leads 46 and 56 of the module 100. The directional fitting may prevent a user from connecting the electrical cables in the wrong way. An electrical charge is then applied to the self-contained gel electrophoresis module 100 by turning on the power supply. As shown in FIG. 2B, the electrical current flows as following: (1) the graphite electrode 45; (2) the buffer 47 in the first chamber 40; (3) the opening 41; (4) the membrane 42; (5) the buffer 84; (6) the first gel matrix 70 (through the second gel matrix 71 if used); (7) the membrane 52; (8) the opening 51; (9) the buffer 57 in the second chamber 50; and (10) the graphite electrode 55.

Figure 12:
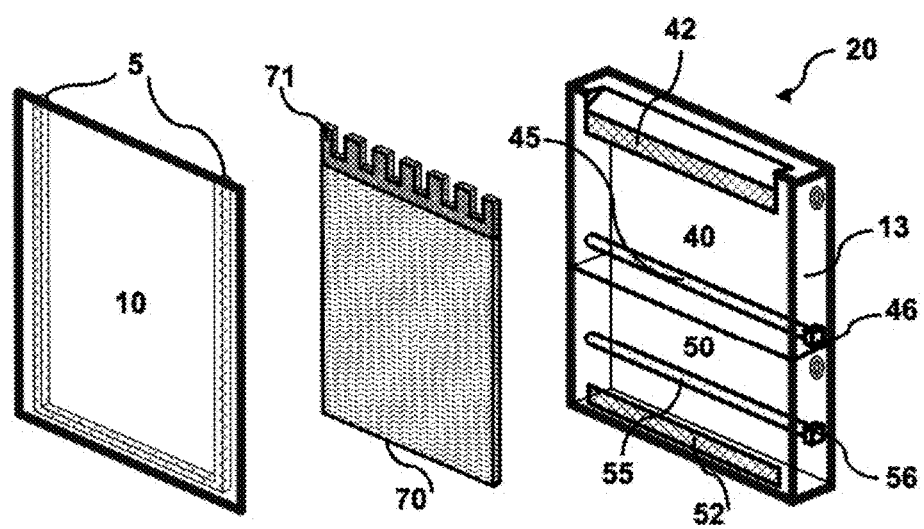
FIG. 12 illustrates a perspective view of the disassembly of an exemplary gel electrophoresis module consistent with the disclosed embodiments.

The gel electrophoresis module 100 may be dissembled to retrieve the gel and the module 100 may be disposable. FIG. 12 illustrates an exemplary dissembled module 100. After electrophoresis is complete, the power supply is turned off, and the power cables 90 from the power supply (not shown) are disconnected from the external leads 46 and 56 of the module 100. The small volume of buffer 84 above the first gel matrix 70 (the second gel matrix 71 if used) is discarded by poured off (or absorption with tissue paper), and the module 100 is disassembled (or pried open) by using a simple lever to initiate separation along the embossed ridge 5. Then, the gel plate 10 can be pulled apart from the buffer chamber box 20, which keeps the buffers intact. The first gel matrix 70 is removed for subsequent analytical procedures. Unlike the conventional electrophoresis, using the system 200 may not involve the steps such as removing the lid from the tank, removing the gels from the cell, discarding the running buffer, and other steps that may be necessary.

EXAMPLE

Figure 13:
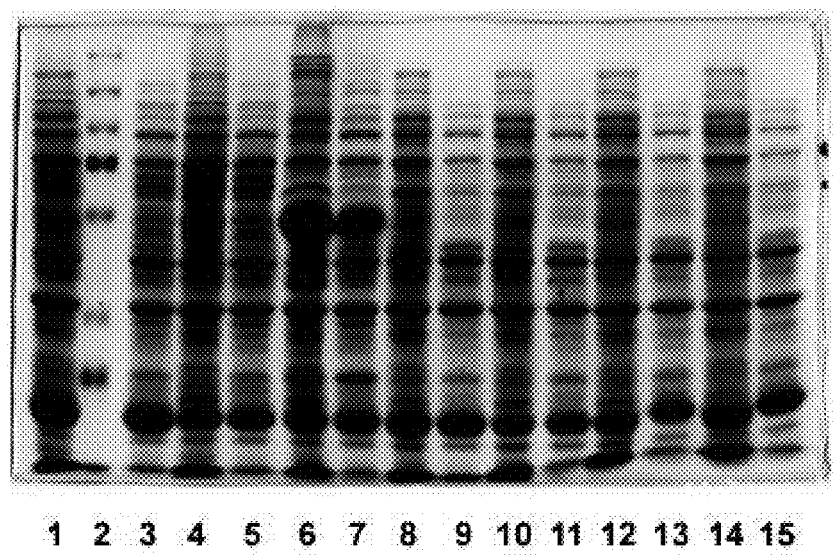
FIG. 13 illustrates an electrophoresis result carried out on an exemplary prefabricated, self-contained gel electrophoresis module and system consistent with the disclosed embodiments.

FIG. 13 shows the results of performing electrophoresis on first gel matrix 70 and second gel matrix 71 using the module 100. The proteins were separated on a polyacrylamide gel constituted by the first gel matrix 70 (12% (w/v) acrylamide, 0.1% (w/v) sodium dodecyl sulfate (SDS), 0.05% (w/v) ammonium persulfate (APS), 0.005% (v/v) N,N,N',N'-tetramethylethylenediamine (TEMED), 0.375 M Tris, pH 8.8) and the second gel matrix 71 (4% (w/v) acrylamide, 0.1% (w/v) SDS, 0.05% (w/v) APS, 0.005% (v/v) TEMED, 0.125 M Tris, pH 6.8). Both cathode and anode buffer solutions were composed of 25 mM Tris, 192 mM glycine, 0.1% SDS. Lane 2 in FIG. 13 shows the protein molecular weight markers. Lanes 1 and 2-15 show whole cell lysate and supernatant samples of $E.$ $coli$ that are either induced or uninduced by isopropyl β-D-1-thiogalactopyranoside (IPTG). The results shown in FIG. 13 were comparable with the results of performing electrophoresis on a neutral pH polyacrylamide gel using the module 100. The neutral polyacrylamide gel constituted by a first gel matrix 70 (12% (w/v) acrylamide, 0.06% (w/v) ammonium persulfate (APS), 0.004% (v/v) TEMED, 0.375 M Bis(2-hydroxyethyl)amino-tris(hydroxymethyl) methane (BIS-TRIS), pH 6.8) and a second gel matrix 71 (4% (w/v) acrylamide, 0.06% (w/v) APS, 0.004% (v/v) TEMED, 0.125 M Tris, pH 6.8). The neutral cathode and anode buffer solutions were composed of 250 mM MOPS 250 mM Tris 5 mM EDTA 0.5% SDS.

While various embodiments in accordance with the present invention have been shown and described, it is understood that the invention is not limited thereto. The present invention may be changed, modified and further applied by those skilled in the art. Therefore, this invention is not limited to the detail shown and described previously, but also includes all such changes and modifications. For example, the size, and shape of the module according to the present disclosure may be adjusted.

We claim:

1. A gel electrophoresis system for performing gel electrophoresis comprising an electrophoresis module, the electrophoresis module comprising:
    a buffer chamber box having a front surface, a top surface, a first side surface, a second side surface, a bottom surface and a back surface, the buffer chamber box being divided into a first chamber and a second chamber by a divider;
    a first opening located on an area of the front surface covering the first chamber and a second opening located on an area of the front surface covering the second chamber;
    a first conductive path member sealing the first chamber at the first opening and a second conductive path member sealing the second chamber at the second opening;
    a first electrode located in the first chamber and a second electrode located in the second chamber;
    a gel plate; and
    a gel chamber formed by the gel plate and the front surface of the buffer chamber box, wherein:
    the buffer chamber box is enclosed by the front surface, the top surface, the first side surface, the second side surface, the bottom surface and the back surface;
    the first conductive path member connects the gel chamber and the first chamber electrically and the second conductive path member connects the gel chamber and the second chamber electrically; and
    the first electrode and the second electrode connects electrically to an external lead located on the side of the buffer chamber.

2. The gel electrophoresis system according to claim 1, further comprising:
    a gel system within the gel chamber having a first gel matrix and a gel buffer.

3. The gel electrophoresis system according to claim 2, further comprising:
    a first buffer in the first chamber; and
    a second buffer in the second chamber.

4. The gel electrophoresis system according to claim 2, further comprising:
    a comb residing on the top of the first gel matrix.

5. The gel electrophoresis system according to claim 1, wherein:
    the first conductive path member is a conductive membrane capable of sealing the first opening.

6. The gel electrophoresis system according to claim 1, further comprising:
    a seal capable of sealing the top of the electrophoresis module.

7. The gel electrophoresis system according to claim 1, wherein:
    the first electrode and the second electrode are graphite electrodes.

8. The gel electrophoresis system according to claim 1, further comprising:
    a conductive lead electrically contacting one of the first electrode and the second electrode, the conductive lead being configured to electrically connected to a power supply.

9. The gel electrophoresis system according to claim 1, wherein:
    the first electrode is located near the divider and the second electrode is located near the middle of the second chamber.

10. The gel electrophoresis system according to claim 1, further comprising:
    an embossed ridge located on one of the gel plate and the front surface of the buffer chamber box, wherein the gel plate can be detachably attached to the buffer chamber box through the embossed ridge.

11. The gel electrophoresis system according to claim 1, wherein:
    a beveled surface is formed on the front surface of the buffer chamber box on an area of the first chamber at the opposite end to the divider.

12. The gel electrophoresis system according to claim 1, further comprising:
    a third opening located on an area of the back surface covering the first chamber and a fourth opening located on an area of the front surface covering the second chamber;
    a third conductive path member sealing the first chamber at the third opening and a fourth conductive path member sealing the second chamber at the fourth opening;
    a second gel plate; and
    a second gel chamber formed by the second gel plate and the back surface of the buffer chamber box, wherein:
    the third conductive path member connects the second gel chamber and the first chamber electrically and the fourth conductive path member connects the second gel chamber and the second chamber electrically.

13. A gel electrophoresis system for performing gel electrophoresis comprising an electrophoresis module, the electrophoresis module comprising:

a first chamber having a first electrode, a first top surface, a first side surface, a second side surface, a first bottom surface, a first back surface, and a first gel surface, wherein the first top surface, the first side surface, the second side surface, the first bottom surface, the first back surface, and the first gel surface enclose the first chamber;

a first opening on the first gel surface;

a first conductive path member sealing the first opening;

a second chamber having a second electrode, a second top surface, a third side surface, a fourth side surface, a second bottom surface, a second back surface, and a second gel surface, wherein the second top surface, the third side surface, the fourth side surface, the second bottom surface, the second back surface, and the second gel surface enclose the second chamber;

a second opening on the second gel surface;

a second conductive path member sealing the second opening;

an embossed ridge detachably connect the first gel surface and the second gel surface; and a gel chamber formed by the embossed ridge as the bottom of the gel chamber, the first gel surface and the second gel surface, wherein the first conductive path member connects the gel chamber and the first chamber electrically and the second conductive path member connects the gel chamber and the second chamber electrically;

the first electrode connects electrically to an external lead located on the first side; and the second electrode connects electrically to an external lead located on the third side.

14. The gel electrophoresis system according to claim 13, further comprising:

a gel system within the gel chamber having a gel matrix and a gel buffer.

15. The gel electrophoresis system according to claim 14, further comprising:

a comb residing on the top of the first gel matrix.

16. The gel electrophoresis system according to claim 13, further comprising:

a first buffer in the first chamber; and a second buffer in the second chamber.

17. The gel electrophoresis system according to claim 13, wherein:

the first conductive path member is a conductive membrane capable of sealing the first opening.

18. The gel electrophoresis system according to claim 13, further comprising:

a seal capable of sealing the top of the electrophoresis module.

19. The gel electrophoresis system according to claim 13, wherein:

the first electrode and the second electrode are graphite electrodes.

20. The gel electrophoresis system according to claim 13, further comprising:

a conductive lead electrically contacting one of the first electrode and the second electrode, the conductive lead being configured to electrically connected to a power supply.

21. The gel electrophoresis system according to claim 13, wherein:

a beveled surface is formed at the top of the first chamber on the first gel surface of the first chamber.

* * * * *